United States Patent [19]

Fuqua

[11] Patent Number: 4,738,666
[45] Date of Patent: Apr. 19, 1988

[54] VARIABLE DIAMETER CATHETER

[75] Inventor: Clark R. Fuqua, Salem, Va.

[73] Assignee: Genus Catheter Technologies, Inc., Roanoke, Va.

[21] Appl. No.: 7,738

[22] Filed: Jan. 28, 1987

Related U.S. Application Data

[60] Division of Ser. No. 872,601, Jun. 10, 1986, Pat. No. 4,710,181, which is a continuation-in-part of Ser. No. 743,705, Jun. 11, 1985, Pat. No. 4,601,713.

[51] Int. Cl.$^4$ .................................... A61M 25/00
[52] U.S. Cl. .................................. 604/280; 604/96; 604/104; 604/265; 128/343
[58] Field of Search ...................... 604/95-96, 604/104, 105-109, 265-268, 280-282, 170; 128/343-344

[56] References Cited

U.S. PATENT DOCUMENTS

| | | | |
|---|---|---|---|
| 2,442,573 | 6/1948 | Stafford | 604/104 |
| 3,460,541 | 10/1966 | Doherty | 128/351 |
| 3,490,457 | 1/1970 | Petersen | 128/349 |
| 3,592,197 | 7/1971 | Cohen | 604/106 |
| 3,598,127 | 8/1971 | Wepsic | 128/349 |
| 3,736,939 | 6/1973 | Taylor | 604/265 |
| 3,789,852 | 2/1974 | Kim et al. | 604/104 |
| 3,877,429 | 4/1975 | Rasumoff | 128/214.4 |
| 4,000,739 | 1/1977 | Stevens | 128/214.4 |
| 4,043,346 | 8/1977 | Mobley et al. | 604/107 |
| 4,141,364 | 2/1979 | Schultze | 128/349 |
| 4,195,637 | 4/1980 | Gruntzig et al. | 128/348 |
| 4,257,422 | 3/1981 | Duncan | 604/282 |
| 4,276,874 | 7/1981 | Wolvek et al. | 128/1 D |
| 4,309,994 | 1/1982 | Grunwald | 604/284 |
| 4,315,512 | 2/1982 | Fogarty | 128/344 |
| 4,327,735 | 5/1982 | Hampson | 128/348 |
| 4,401,433 | 8/1983 | Luther | 604/159 |
| 4,406,656 | 9/1983 | Hattler et al. | 604/158 |
| 4,411,655 | 10/1983 | Schreck | 604/165 |
| 4,451,256 | 5/1984 | Weikl et al. | 128/343 |
| 4,467,790 | 8/1984 | Schiff | 128/1 D |
| 4,493,711 | 1/1985 | Chin et al. | 604/271 |
| 4,498,902 | 2/1985 | Ash et al. | 604/164 |
| 4,563,176 | 1/1986 | Gustavsson et al. | 604/163 |
| 4,564,014 | 1/1986 | Fogarty et al. | 128/344 |
| 4,573,931 | 3/1986 | McFarlane | 604/263 |
| 4,601,713 | 7/1986 | Fuqua | 604/280 |

FOREIGN PATENT DOCUMENTS 1001034 12/1976 Canada .
86338 8/1983 European Pat. Off. .
1810804 6/1970 Fed. Rep. of Germany .

OTHER PUBLICATIONS

Roy A. Tucker–"History of Sizing of Genitourinary Instruments", *Urology*, Sep. 1982, vol. XX, No. 3, pp. 346-349.
Newman et al, "A General Ureteral Dilated-Sheathing System", *Urology*, vol. XXV, No. 3, Mar. 1985, pp. 287-288.

*Primary Examiner*—C. Fred Rosenbaum
*Assistant Examiner*—Gene B. Kartchner
*Attorney, Agent, or Firm*—Isaksen, Lathrop, Esch, Hart & Clark

[57] ABSTRACT

The present invention provides a variable diameter catheter which is folded in a longitudinal manner in order to reduce the diameter for convenient and less traumatic insertion into a body orifice. The fold in the catheter is maintained by a slidably removable external sheath which aids in insertion of the catheter and in dispersion of an anti-infective medication. Once the catheter is placed in the body orifice, the external sheath is removed. The present invention is also directed to the external sheath.

5 Claims, 2 Drawing Sheets

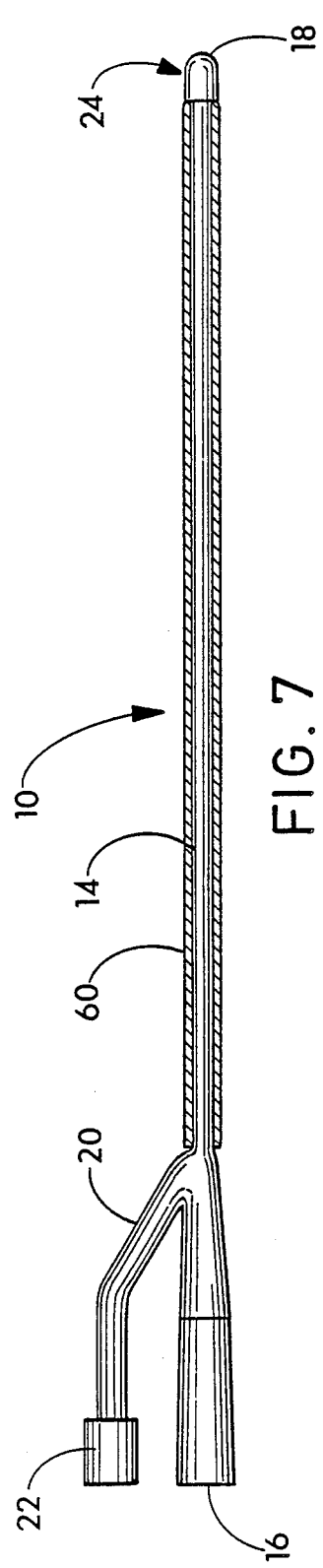
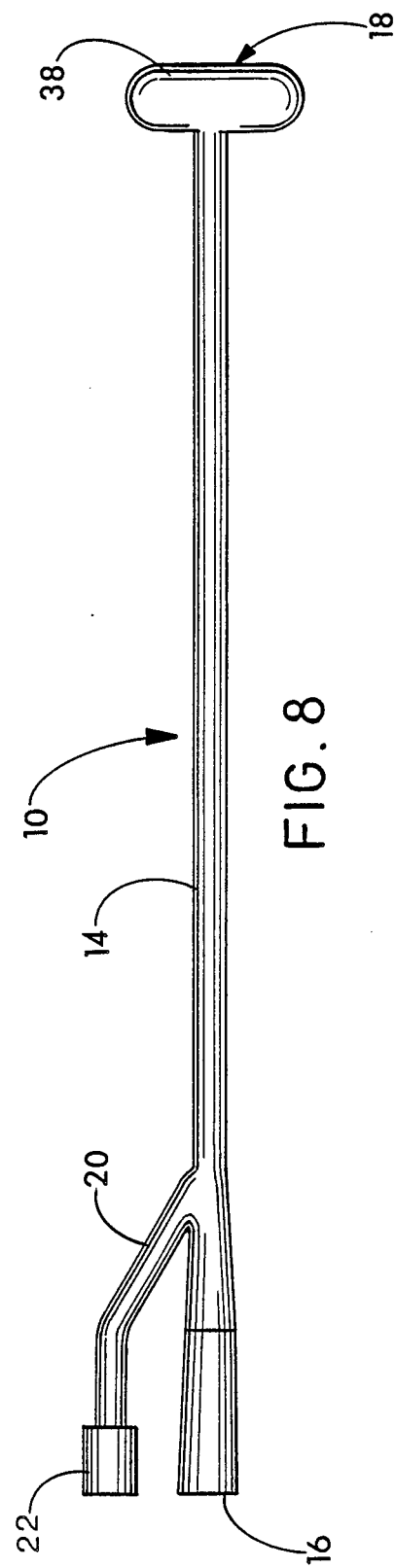

VARIABLE DIAMETER CATHETER

CROSS REFERENCE TO RELATED APPLICATION

This is a division, of application Ser. No. 872,601, now U.S. Pat. No. 4,710,181 filed June 10, 1986, which is a continuation-in-part of application Ser. No. 743,705, filed June 11, 1985, now U.S. Pat. No. 4,601,713.

BACKGROUND OF THE INVENTION

1. Field of the Invention

The present invention is generally directed to medical catheters, and specifically directed to a variable diameter catheter (VDC) in which the diameter of the catheter is decreased for insertion into a body cavity.

2. Description of Prior Art

Catheters are ubiquitous to the medical field, finding importance in a variety of uses. The term "catheter" is commonly used to identify a tubular instrument that is inserted into a body cavity or orifice, naturally or surgically opened, and the catheter of the present invention will be understood as intended thus broadly unless the context clearly indicates the contrary. The following list indicates the broad range of uses for catheters:

1. intravenous cannula
2. umbilical catheters
3. endotracheal tubes
4. suction catheters
5. oxygen catheters
6. stomach tubes
7. feeding tubes
8. lavage tubes
9. rectal tubes
10. urological tubes
11. irrigation tubes
12. trocar catheters
13. heart catheters
14. aneurysm shunts
15. stenosis dilators A history of catheters is presented in parent application Ser. No. 743,705 now U.S. Pat. No. 4,601,713 to Fuqua, which has been incorporated herein by reference, and will not be duplicated in this application. It will suffice to summarize that the present technology relating to catheterization is documented to be the cause of many infection-related problems associated in the medical industry. However, it is still considered to be the lesser of two evils. On the one hand, if the physician does not catheterize a patient, the patient may develop or experience further medical difficulties. On the other hand because catheters are readily available and very common, a physician will undoubtedly insert a catheter and risk the resulting infection.

My parent application Ser. No. 743,705 now U.S. Pat. No. 4,601,713 describes a method and apparatus for producing and using a variable diameter catheter in which the diameter of the catheter is reduced by about one-half for insertion into a body orifice with a minimum of discomfort and difficulty. The wall of the catheter is longitudinally folded upon itself or involuted in order to reduce the overall diameter of the catheter for insertion. The reduced-diameter catheter is held in place by a retaining means placed in the lumen of the catheter.

Until the present invention was developed, it was not thought possible to provide a variable diameter catheter with an external retaining means. At best, the prior art appears to disclose catheters with external housings serving a variety of purposes generally unrelated to the present invention.

For example, U.S. Pat. No. 4,401,433 to Luther is directed to longitudinally folding an oversized catheter by introducing it in a folded state into a cannula. The wall of the catheter does not vary in thickness. The cannula then penetrates a vein and the catheter is inserted into the vein in folded condition. Due to the resiliency of the catheter, the catheter expands into its normal shape as it leaves the cannula. The cannula is then retracted. U.S. Pat. No. 4,411,655 to Schreck discloses the introduction of a reduced diameter catheter. The catheter comprises a "shape memory alloy" which allows the catheter to be at a reduced diameter at one temperature and at a larger diameter at another higher temperature. The catheter is surrounded by a protective sheath. However, there is no fold in the catheter, nor is the sheath removable. U.S. Pat. No. 3,877,429 to Rasumoff is directed to a catheter placement device which is a flexible cannula stiff enough to provide structural support during placement of the catheter. In this case the cannula is first inserted into the blood vessel, and then the catheter is threaded through the cannula causing the cannula to split. The cannula is then withdrawn leaving the catheter in place.

Other patents show sheaths surrounding a catheter in one form or another. For example, Canadian Patent 1,001,034 to McWhorter discloses a suprapubic catheter and a hollow-needle combination. In its natural state, i.e., in the bladder, the catheter is coiled. The hollow needle is meant to introduce the catheter into the bladder. The needle straightens the catheter out but, due to the catheter memory, the coil is regained once the catheter leaves the needle and enters the bladder.

European Patent Application Publication No. 86,338 to Wonder et al is directed to a flexible inner catheter tube which is slidably positioned within a more rigid, outer catheter sheath tube. The sheath gives rigidity to the catheter during the insertion of the catheter into a body orifice. The outer sheath is then retracted after insertion of the catheter at the injection site. Thus, the outer sheath never actually enters the body orifice.

U.S. Pat. No. 4,000,739 to Stevens discloses a hemostasis catheter. The catheter includes a hollow plastic dilator which is slipped over a guide. A hole in the vessel wall is dilated and a tube inside the dilator enters the lumen of the blood vessel. The dilator and guide are then removed and the catheter is inserted into the vessel.

U.S. Pat. No. 4,564,014 to Fogarty et al discloses a dilation catheter with a telescopic sheath to expose varying lengths of the catheter for inflation.

U.S. Pat. No. 4,573,981 to McFarlane discloses a catheter and protective sheath which prevents damage to the catheter. The sheath is removed prior to insertion of the catheter.

U.S. Pat. No. 3,598,127 to Wepsic discloses a catheter which provides an antibacterial substance throughout the length of the tube. The catheter has an inner tube of nonpermeable rubber formed with V-grooves along the length of the outside of the tube. The grooves carry the antibacterial substance. A permeable polysiloxane rubber sheath surrounds the grooves in order to allow diffusion of the medicine.

U.S. Pat. No. 4,498,902 to Ash et al discloses a catheter guide which is placed in the body through a trocar. The catheter is then introduced through the guide.

U.S. Pat. No. 4,563,176 to Gustavsson et al discloses a protective sheath and catheter. The protective sheath is a plastic bag providing a sterile environment for the catheter.

U.S. Pat. No. 4,327,735 to Hampson discloses a catheter in a collapsible protective sheath. As the catheter enters the body, the sleeve collapses outside the body in accordian-like pleats. The catheter is withdrawn inside the sleeve.

Although some catheter protector sheaths are disclosed in the prior art, it would be advantageous to provide a catheter which has a reduced diameter for insertion into a body orifice and which is provided with a means for both maintaining the reduced diameter and aiding the spread of an anti-infection medicament around the catheter.

OBJECTS OF THE INVENTION

It is an object of the invention to produce a medical catheter which reduces problems relating to infection and patient trauma.

It is also an object of the present invention to produce a catheter which is insertable into a body orifice with a minimum of discomfort and difficulty.

It is further an object of the present invention to produce a catheter in which the diameter of the catheter tube is folded to reduce the overall diameter of the catheter during the insertion process.

Further, it is an object of the present invention to produce a catheter which will aid in the spread of an anti-infective medicament within the body orifice.

It is further an object of the invention to produce a catheter which can be inserted into a body orifice without requiring an internally placed stylet.

These and other objects will be addressed in the following sections.

SUMMARY OF THE INVENTION

The present invention provides a variable diameter catheter adapted to be inwardly folded in a longitudinal manner, comprising a resiliently flexible tube of generally uniform diameter along the length of the tube. When viewed in cross section, the wall of the tube varies in thickness, such that the portion of the wall which folds inwardly is thinner than the rest of the wall.

The present invention is also directed to a flexible, thin-membrane tubular sheath which surrounds the catheter tube during placement of the catheter in a body orifice. The sheath serves the purpose of retaining the fold in a folded variable diameter catheter and it aids in dispersing an anti-infection medicament in order to prevent infection resulting from the placement of a catheter in a body orifice.

The present invention is also directed to a method of inserting a variable diameter catheter in a body orifice in which the catheter is folded and held in a folded state by an external sheath surrounding the catheter.

BRIEF DESCRIPTION OF THE DRAWINGS

FIG. 7 is a side view of the catheter of the present invention with the external retaining means in position; and FIG. 8 is a side view of the catheter of the present invention with the external retaining means removed.

DETAILED DESCRIPTION OF THE INVENTION

The present invention is directed to the concept that inserting a smaller diameter catheter into a body orifice will create less trauma to the patient, thereby reducing the risk of infection and the painful effects of catheter placement. The term "body orifice" or "body cavity" is meant to include a natural or surgically prepared body opening. Examples of natural body orifices include the urethral tube, ureter, blood vessels, esophagus and the like. Additionally, a body orifice may be reached percutaneously or by puncture. Further benefits of the present invention will be more thoroughly discussed hereinafter. The VDC will now be described with reference to the figures.

Figure 1:
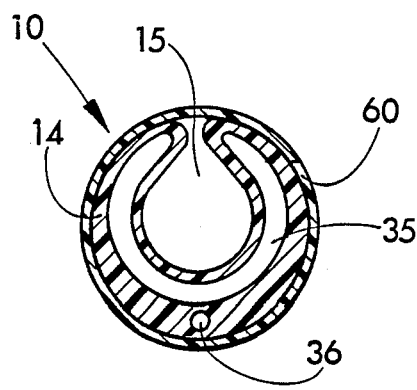
FIG. 1 and 2 are enlarged, cross-sectional views of a preferred embodiment of the catheter tube of the present invention in the folded position (FIG. 1) and in the fully expanded or rounded catheter position (FIG. 2)
Figure 2:
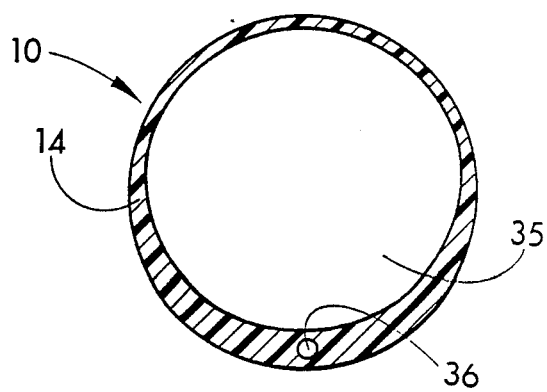
Figure 3:
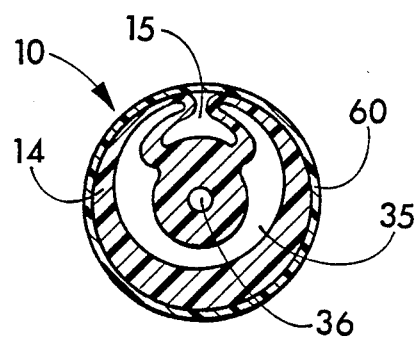
FIGS. 3 and 4 are enlarged, cross-sectional views of a different embodiment of the catheter tube of the present invention in the folded position (FIG. 3) and in the fully expanded position (FIG. 4)
Figure 4:
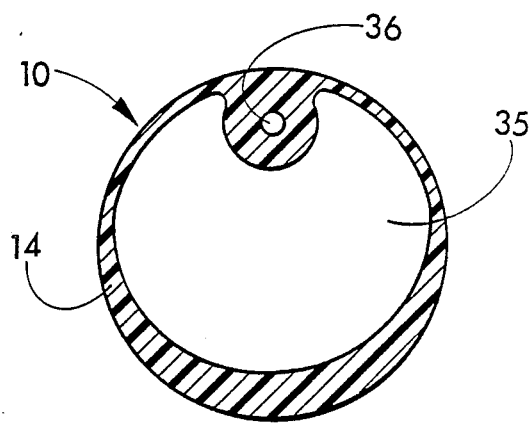

FIGS. 1–4 are cross-sectional illustrations of different embodiments of VDC 10 in various stages of expansion, from the folded position (FIGS. 1 and 3) to the fully expanded or rounded positions (FIGS. 2 and 4). A detailed description of VDC 10 is presented in U.S. patent application Ser. No. 743,705. VDC 10 comprises a flexible plastic tube 14 which may be composed of any standard flexible, non-toxic material used for catheter production, such as, for example, natural rubber or latex, polypropylene, polyethylene, polyvinyl chloride or silicone. It is desired that the surface of tube 14 be coated with a low friction material such as, for example, TEFLON (Reg. TM) in order to eliminate the tendency to grab the mucous tissues and to prevent a buildup of infection-causing organisms.

As seen from the cross-sectional views, VDC 10 includes drainage lumen 35 and inflation lumen 36. Inflation lumen 36 runs the length of VDC 10 from an inflation valve to an inflation diaphragm or balloon (seen in FIGS. 7 and 8). Inflation lumen 36 can be housed within the section of the catheter wall creating the fold 15 of VDC 10 as shown in FIGS. 3 and 4, or it can be located in the thickest part of the wall of tube 14 as illustrated in FIGS. 1 and 2. Inflation lumen 36 acts as an inflation fluid conduit for inflating a diaphragm or balloon 38, shown in FIG. 8. Drainage lumen 35 runs the length of catheter tube 14.

As illustrated in FIGS. 1 and 3, a means for holding the longitudinal fold of tube 14 in place is an external retaining means or sheath 60. Sheath 60 is preferably a flexible sheath comprising a tubular wall slidably and removably placed on catheter tube 14 when the catheter tube is in the involuted or folded stage. Sheath 60 may be made of a hard plastic tube if an occasion for this use arises. Generally, sheath 60 may be made of any of a variety of non-toxic materials having a high doxemeter rating to prevent unfolding of the folded VDC when the sheath is in place. Doxemeter is a measure of the tensile strength of the material. By a high doxemeter rating is meant high resilience and resistance to stretching. For example, a sheath for the purposes of the present invention should have a doxemeter reading of at least about 65%. This is compared to a standard balloon such as, for example, inflation balloon 38, which has a doxemeter rating of about 35. The lower the doxemeter number, the greater the degree of stretching or elasticity.

For purposes of the present invention, it is important that the tubular sheath be made of the thinnest material which will accept the conditions expressed above. Generally, the thickness of the sheath wall should be approximately 0.008 inches. It has been found that materials such as silicone, TEFLON (Reg. TM) natural rubber or latex can be extruded in a manner acceptable for the purposes of the present invention.

The removable sheath 60 is adapted to surround tube 14 during placement of VDC 10 into a body orifice in such a manner that the sheath can be removed after the catheter is in place. Removal can be accomplished simply by pulling the sheath at the proximal end of the tube thereby removing the sheath from the tube and allowing the tube to expand to full size as a result of the memory of the system. Advantageously, the presently described VDC does not require an internal stylet, and thus a stylet does not have to be removed after the VDC has been inserted.

Figure 5:
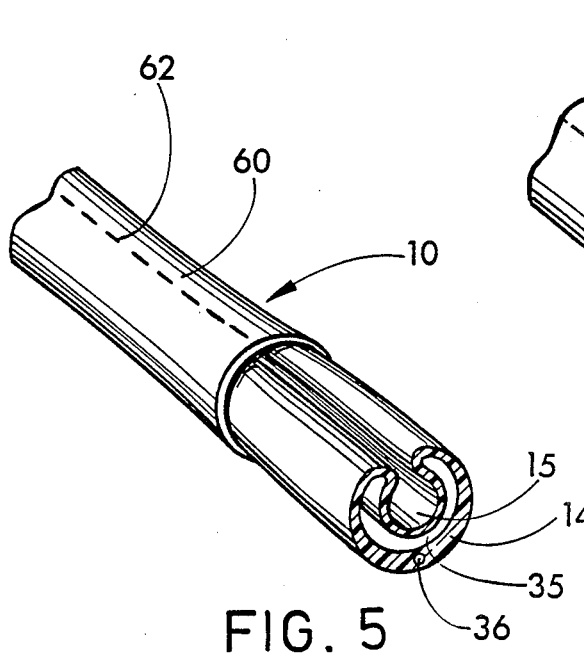
FIG. 5 is a perspectve view of the folded catheter of the present invention with the external retaining means partially in place.
Figure 6:
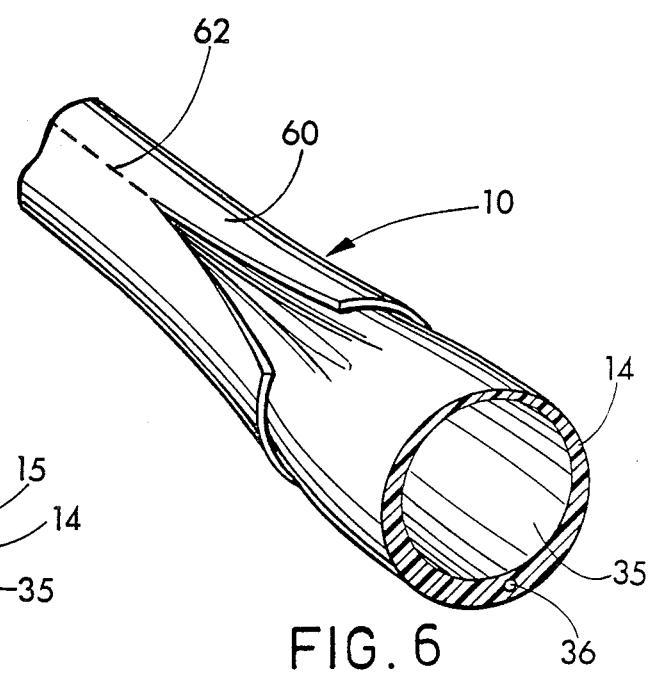
FIG. 6 is a perspective view of the catheter of the present invention as it is expanding to full size and consequently tearing the external retaining means along perforations.

FIGS. 5 and 6 show another illustration of the VDC/external retaining means combination. FIG. 5 discloses a partially constructed view of folded tube 14 with sheath 60 retaining the fold. In order to allow for expansion of tube 14, sheath 60 need merely to be removed by sliding the catheter from tube 14. Alternatively, and preferably, sheath 60 is provided with perforations 62 running the length of the sheath. As sheath 60 is removed from tube 14 allowing tube 14 to expand, the expansion causes sheat 62 to separate at the perforations, as illustrated in FIG. 6. This facilitates the removal of sheath 60 from tube 14.

FIGS. 7 and 8 disclose an entire embodiment of VDC 10. FIG. 1 represents a folded VDC 10 with sheath 60 in position. For reference purposes, the proximal end of VDC 10 is marked at reference numeral 16 and the distal end at 18. Tube 14 is fixedly attached to inflation tube 20, located near proximal end 16 of VDC 10. Located at the proximal end of inflation tube 20 is inflation valve 22 which is designed to accept a luer tip syringe (not shown). Distal end 18 is occluded by a removable cap 24, such as a gelatin cap, which is discussed more thoroughly in parent application Ser. No. 743,705.

When sheath 60 is positioned around VDC 10, as shown in FIG. 7, the external diameter of tube 14 is reduced by approximately one-half.

In order to remove sheath 60 from VDC 10, the sheath is slidably pulled toward proximal end 16 thereby allowing VDC 10 to start unfolding at distal end 18. The pressure of opened tube as it is unfolding from the tube will facilitate removal of sheath 60 as it is being pulled. As mentioned previously, sheath 60 may include perforations 62 which will further facilitate removal of the sheath.

Removal of sheath 60 can then be facilitated by inflating inflation balloon 38, as shown in FIG. 8. Inflation lumen 36 acts as an inflation fluid conduit for inflating balloon 38. In this embodiment, it is desirable to surround balloon 38 in its deflated state with the distal portion of sheath 60. When balloon 38 is then inflated, it will initiate a tear in sheath 60 at the perforations thus facilitating removal of the sheath from the VDC. As tube 14 expands to its normal or fully expanded diameter, due to the memory of the tubular system, the sheath will continue to tear away at the perforations in a zipper-like fashion.

The VDC of the present invention is well adapted to be used for virtually any purpose known for catheter technology and in virtually any size. This includes use as a urological catheter, feeding tube, percutaneous catheter, kidney tubes, cardiovascular catheters, and catheters for removing strictures or occlusions in veins or other body orifices. A non-limiting example of utilizing a VDC follows.

For urological purposes, there are two prevalent techniques for inserting a catheter into the urinary bladder. One technique is to insert the catheter through the urethra. The catheter in its folded state with the external retaining means in place is inserted through the urethra in such a manner that the tip of the catheter and the portion including the balloon is inserted into the bladder. At this point, the balloon is inflated in order to secure the catheter. The sheath may then be simply removed by sliding it away from the bladder out of the body orifice. Alternatively, and preferably, as the inflation balloon is inflated, this will create an initial tear at the perforation site of the sheath. Then, as the sheath is being removed, the combination of the initial tear and the unfolding of the catheter will further tear the sheath at the perforations allowing the sheath to be more easily removed.

As mentioned previously, the catheter of the present invention can be adapted for use in a blood vessel or as a chest tube. Within certain limits, the size of the body orifice is not a factor.

The advantages of the catheter of the present invention are several. First, the insertion process of the catheter is much eaier. A catheter which is almost pediatric in size, i.e., a Frensh size of 9, can be inserted into an adult. The insertion of a smaller tube is less traumatic and painful, and will cause much less scoring, stretching and scarring of the body tissue during the insertion process. It should also reduce the infection rate.

Further, by inserting a catheter one-half the approximate unfolded size into a body orifice, and then adjusting the diameter of the tube, the diameter of the catheter tube can be brought up to the diameter of the body orifice, which is far less painful and much less damaging to the interior surface of the body orifice, as compared to inserting the catheter tube at its maximum diameter.

Another advantage of the catheter of the present invention over that of the prior art is directed to the application of an anti-infective medication into the body orifice as the catheter is being placed therein in order to reduce the chances of infection. It is well known that one way to combat infection is to coat a catheter tube with an anti-infection medication. However, with full diameter catheters the catheter tubes fit tightly into the body orifice causing the anti-infection medication to rub off at the entrance or the body orifice. Therefore, it can be expected that the entrance of proximal end of the body orifice has a buildup of anti-infection medication, while the distal end of the body orifice will receive virtually no medication. With the catheter of the present invention, the antifection medication may be placed in fold 15 of catheter tube 14. Because the catheter tube is folded during the insertion process and the sheath surrounding the catheter tube protects that fold, fold 15 shields the anti-infection medication so that it is not removed during the insertion process. Once the tube is inserted into the bladder, the catheter is allowed to resume its normal shape. The anti-infection medicine is thus pushed out of fold 15 and spread around the catheter tube. Therefore, the anti-infection medication will completely surround all of catheter tube 14. Non-limiting examples of anti-infection medication include heparin and iodine.

Although the present invention has been described with preferred embodiments, it is understood that modifications and variations may be resorted to, without departing from the spirit and scope of this invention, as those skilled in the art will readily understand.

I claim:

1. A variable diameter catheter adapted to be folded in a longitudinal manner, comprising a resiliently flexible tube of generally uniform diameter along the length of said tube, said tube in cross-section having a single, external wall of varying thickness, such that the portion of said wall which is adapted to fold is thinner than the rest of said wall.

2. The catheter according to claim 1, wherein said tube includes a drainage lumen and an inflation lumen.

3. The catheter according to claim 2, wherein said flexible tube includes a proximal end, a distal end, and an inflatable diaphragm disposed adjacent said distal end, said inflation lumen connecting said diaphragm to an opening in said proximal end of said tube, said inflation lukmen being independent of said drainage lumen, and being adapted to selectively and independently admit and exhaust fluid from said diaphragm.

4. The catheter according to claim 3, wherein said distal end is provided with a single opening communicating with said drainage lumen.

5. A method for inserting a catheter tube into a body orifice comprising:

(a) folding said catheter tube along its longitudinal length, wherein the diameter of said folded catheter tube is substantially smaller than the diameter of said catheter tube in unfolded state, said tube being provided with a memory of a normal distended configuration, said folding being conducted and held by an exteriorly placed fold retaining means;
 (b) inserting said folded catheter tube into said body orifice; and
 (c) slidably removing said exteriorly placed fold retaining means from said folded catheter tube thus causing said folded catheter tube to unfold.

* * * * *